(12) United States Patent
Adler et al.

(10) Patent No.: US 7,585,273 B2
(45) Date of Patent: Sep. 8, 2009

(54) WIRELESS DETERMINATION OF ENDOSCOPE ORIENTATION

(75) Inventors: Doron Adler, Nasher (IL); David Hanuka, Ramet Yishay (IL); Shai Finkman, Haifa (IL); Frank D'Amelio, Santa Barbara, CA (US)

(73) Assignee: C2Cure, Inc., Wilmington, DE (US)

( * ) Notice: Subject to any disclaimer, the term of this patent is extended or adjusted under 35 U.S.C. 154(b) by 778 days.

(21) Appl. No.: 11/211,327

(22) Filed: Aug. 24, 2005

(65) Prior Publication Data

US 2006/0074289 A1 Apr. 6, 2006

Related U.S. Application Data

(60) Provisional application No. 60/605,233, filed on Aug. 26, 2004.

(51) Int. Cl.
*A61B 1/00* (2006.01)
(52) U.S. Cl. .................. 600/117; 600/118; 600/424; 600/407; 600/109
(58) Field of Classification Search .............. 600/109, 600/117, 118, 407, 424; 382/128
See application file for complete search history.

(56) References Cited

U.S. PATENT DOCUMENTS

| | | | |
|---|---|---|---|
| 4,061,135 A | 12/1977 | Widran et al. | |
| 4,140,364 A | 2/1979 | Yamashita et al. | |
| 4,248,213 A | 2/1981 | Landre | |
| 4,697,577 A | 10/1987 | Forkner | |
| 4,858,001 A | 8/1989 | Milbank et al. | |
| 4,880,011 A | 11/1989 | Imade et al. | |
| 4,924,853 A | 5/1990 | Jones, Jr. et al. | |
| 5,005,943 A | 4/1991 | Fort | |
| 5,224,467 A | 7/1993 | Oku | |
| 5,280,871 A | 1/1994 | Chuang et al. | |
| 5,307,804 A | 5/1994 | Bonnet | |
| 5,540,650 A | 7/1996 | Smith | |
| 5,545,120 A | 8/1996 | Chen et al. | |
| 5,588,948 A | 12/1996 | Takahashi et al. | |
| 5,671,748 A * | 9/1997 | Itoi | 600/462 |
| 5,699,805 A | 12/1997 | Seward et al. | |
| 5,701,900 A | 12/1997 | Shehada et al. | |

(Continued)

FOREIGN PATENT DOCUMENTS

JP  5168635  7/1993

(Continued)

OTHER PUBLICATIONS

U.S. Appl. No. 60/605,233.

(Continued)

*Primary Examiner*—John P Leubecker
*Assistant Examiner*—Samuel Candler
(74) *Attorney, Agent, or Firm*—Ganz Law, P.C.

(57) ABSTRACT

Apparatus for performing a medical procedure includes an invasive probe having opposite distal and proximal ends. The probe includes a transmitter, which is arranged to transmit an energy field, and a receiver, which is arranged to receive the energy field, wherein the transmitter and the receiver are disposed at the opposite ends of the probe. A control unit is adapted to determine an orientation of the distal end relative to the proximal end responsively to the energy field received by the receiver.

17 Claims, 3 Drawing Sheets

U.S. PATENT DOCUMENTS

| | | | |
|---|---|---|---|
| 5,720,706 A | 2/1998 | Takahashi et al. | |
| 5,797,836 A | 8/1998 | Lucey et al. | |
| 5,899,851 A | 5/1999 | Koninckx | |
| 6,016,439 A * | 1/2000 | Acker | 600/411 |
| 6,083,170 A * | 7/2000 | Ben-Haim | 600/463 |
| 6,097,423 A | 8/2000 | Mattsson-Boze et al. | |
| 6,221,007 B1 | 4/2001 | Green | |
| 6,248,074 B1 * | 6/2001 | Ohno et al. | 600/463 |
| 6,259,806 B1 * | 7/2001 | Green | 382/128 |
| 6,272,371 B1 | 8/2001 | Shlomo | |
| 6,425,857 B1 | 7/2002 | Rudischhauser et al. | |
| 6,464,631 B1 | 10/2002 | Girke et al. | |
| 6,471,637 B1 | 10/2002 | Green et al. | |
| 6,478,743 B1 | 11/2002 | Jordfald et al. | |
| 6,484,118 B1 | 11/2002 | Govari | |
| 6,626,828 B2 | 9/2003 | Dohi et al. | |
| 6,636,254 B1 | 10/2003 | Onishi et al. | |
| 6,648,817 B2 | 11/2003 | Schara et al. | |
| 6,663,559 B2 | 12/2003 | Hale et al. | |
| 6,695,774 B2 | 2/2004 | Hale et al. | |
| 6,749,572 B2 | 6/2004 | Edwardsen et al. | |
| 6,950,689 B1 * | 9/2005 | Willis et al. | 600/407 |
| 7,020,512 B2 * | 3/2006 | Ritter et al. | 600/434 |
| 7,258,664 B2 * | 8/2007 | Nishimura et al. | 600/117 |
| 2002/0065455 A1 | 5/2002 | Ben-Haim et al. | |
| 2002/0099263 A1 | 7/2002 | Hale et al. | |
| 2002/0133077 A1 | 9/2002 | Edwardsen et al. | |
| 2002/0161280 A1 | 10/2002 | Chatenever et al. | |
| 2003/0032863 A1 | 2/2003 | Kazakevich | |
| 2003/0092966 A1 | 5/2003 | Schara et al. | |
| 2003/0092997 A1 | 5/2003 | Edwardsen et al. | |
| 2003/0114730 A1 | 6/2003 | Hale et al. | |
| 2003/0135112 A1 * | 7/2003 | Ritter et al. | 600/424 |
| 2003/0228039 A1 * | 12/2003 | Green | 382/128 |
| 2003/0229268 A1 | 12/2003 | Uchiyama et al. | |
| 2004/0127769 A1 | 7/2004 | Hale et al. | |
| 2004/0176691 A1 | 9/2004 | Edwardsen et al. | |
| 2005/0027167 A1 * | 2/2005 | Chatenever et al. | 600/173 |
| 2005/0154260 A1 * | 7/2005 | Schara et al. | 600/117 |

FOREIGN PATENT DOCUMENTS

| | | |
|---|---|---|
| JP | 6208061 | 7/1994 |
| JP | 6237881 | 8/1994 |
| JP | 6269403 | 9/1994 |
| JP | 6269406 | 9/1994 |
| JP | 6319697 | 11/1994 |
| JP | 7246183 | 9/1995 |
| JP | 10192233 | 7/1998 |
| JP | 2000227559 | 8/2000 |
| JP | 2000287921 | 10/2000 |
| JP | 2001078960 | 3/2001 |
| JP | 2003225201 | 8/2003 |
| WO | WO 03/098913 | 11/2003 |

OTHER PUBLICATIONS

Israeli Office Action dated Dec. 16, 2008, issued for corresponding Israel patent application No. IL 170404—Hebrew language and English translation are provided; 6 pages total.

* cited by examiner

WIRELESS DETERMINATION OF ENDOSCOPE ORIENTATION

CROSS-REFERENCE TO RELATED APPLICATION

This application claims the benefit of U.S. Provisional Patent Application 60/605,233, filed Aug. 26, 2004, whose disclosure is incorporated herein by reference.

BACKGROUND OF THE INVENTION

During endoscopic procedure using a flexible endoscope, the shape of the endoscope is typically deformed due to constraints of the body passages through which the endoscope must pass, as well as to steering of the endoscope by the operator. As a result, the operator may have difficulty in determining the actual orientation of the distal end of the endoscope, and may therefore be unable to correctly associate the positions of objects seen in endoscopic images with the actual locations of the objects in the patient's body.

In response to these problems, methods have been proposed for measuring the orientation of the endoscope, and then rotating the endoscopic image optically, mechanically or electronically to compensate for the orientation. Exemplary methods for such purposes are described in U.S. Pat. Nos. 6,478,743, 5,545,120, 6,471,637, 6,097,423, U.S. Patent Application Publication 2002/0161280, and U.S. Pat. No. 6,663,559, whose disclosures are incorporated herein by reference. Measurements of the orientation of an invasive probe, such as an endoscope or catheter, may also be used in controlling other types of procedures carried out inside the body using the probe.

SUMMARY OF THE INVENTION

In methods known in the art for determining orientation of an invasive probe, the orientation (and location) of the distal end of the probe is generally measured relative to an external frame of reference, which is separate from the probe itself. For example, a magnetic sensor in the probe may be used to determine the probe orientation relative to a set of magnetic field generators placed in known locations outside the patient's body.

By contrast, in some embodiments of the present invention, the orientation of the distal end of a probe is measured relative to the proximal end of the probe itself, by wireless transmission of an energy field between the distal and proximal ends. Measuring the orientation of the distal end of the probe relative to the proximal end, rather than relative to an external frame of reference, obviates the need for external measurement appliances in order to define the frame of reference. The measured, relative orientation of the distal end of the probe is then used in controlling an aspect of an endoscopic procedure. For example, endoscopic images captured by the probe may be rotated to compensate for the orientation. Since the proximal end of the probe is located outside the body, the operator knows the orientation of the proximal end, so that the relative orientation of the distal end is sufficient for some purposes. Alternatively, the absolute orientation of the proximal end of the probe may be measured relative to an external frame of reference, and the orientation of the distal end in the external frame may then be calculated by combining the relative and absolute measurements.

In some embodiments of the present invention, the measured orientation of the distal end of the probe is used in tracking an imaging scan of the inner surface of a body cavity. A system controller tracks and maps the areas of the surface that have been imaged by the endoscope. The map is presented graphically to the operator of the endoscope, and thus enables the operator to see which areas have not yet been imaged and to steer the endoscope accordingly. Alternatively, the controller may automatically steer the endoscope so as to image the entire surface or a desired area of the surface. The orientation of the distal end may be measured for this purpose using the relative measurement technique described above or, alternatively, using any other suitable method of orientation tracking.

There is therefore provided, in accordance with an embodiment of the present invention, a method for performing a medical procedure using an invasive probe having distal and proximal ends, the method including:

determining an orientation of the distal end relative to the proximal end by wireless transmission of an energy field between the distal and proximal ends; and controlling an aspect of the procedure responsively to the orientation.

Determining the orientation may include transmitting the energy field from a transmitter in the proximal end and sensing the energy field using a receiver in the distal end, or transmitting the energy field from a transmitter in the distal end and sensing the energy field using a receiver in the proximal end. In a disclosed embodiment, the energy field includes an electromagnetic field.

In some embodiments, the method includes inserting the distal end of the probe into a body of a patient, and capturing an image of an area inside the body in proximity to the distal end, wherein controlling the aspect includes rotating the image responsively to the orientation. In one embodiment, determining the orientation of the distal end relative to the proximal end includes finding a first orientation, and rotating the image includes finding a second orientation of the proximal end of the probe relative to a predefined frame of reference, and rotating the image responsively to the first and second orientations so as to orient the image relative to the predefined frame of reference.

In some embodiments, the probe includes a handle at the proximal end thereof, and determining the orientation includes finding the orientation of the distal end relative to the handle.

There is also provided, in accordance with an embodiment of the present invention, apparatus for performing a medical procedure, including:

an invasive probe having opposite distal and proximal ends, the probe including a transmitter, which is arranged to transmit an energy field, and a receiver, which is arranged to receive the energy field, wherein the transmitter and the receiver are disposed at the opposite ends of the probe; and a control unit, which is adapted to determine an orientation of the distal end relative to the proximal end responsively to the energy field received by the receiver.

There is additionally provided, in accordance with an embodiment of the present invention, apparatus for endoscopy, including:

an endoscope, which includes:
 an insertion tube, having distal and proximal ends;
 an imaging assembly within the distal end of the insertion tube, for capturing images of objects in proximity to the distal end;
 a handle, fixed to the proximal end of the insertion tube; and
 a field transmitter and a field receiver, one disposed within the handle and the other disposed within the distal end of the insertion tube;

a display, for displaying the images captured by the imaging assembly; and a control unit, which is coupled to drive the field transmitter to transmit an energy field, and is coupled to receive signals from the field receiver responsively to the energy field transmitted by the field transmitter, and which is adapted to determine an orientation of the distal end of the insertion tube relative to the handle based on the signals and to rotate the images responsively to the orientation.

There is further provided, in accordance with an embodiment of the present invention, a method for imaging a cavity using an endoscope having a distal end, the method including:

inserting the distal end of the endoscope into the cavity;

manipulating the distal end of the endoscope within the cavity so as to capture images of areas of an inner surface of the cavity at multiple, respective viewing angles;

measuring an orientation of the viewing angle while capturing the images; and mapping the areas of the inner surface that have been imaged by the endoscope responsively to the measured orientation.

There is moreover provided, in accordance with an embodiment of the present invention, an endoscopic imaging system, including:

an endoscope which includes:

an insertion tube, having a distal end, which is adapted to be inserted into a cavity;

an imaging assembly within the distal end of the insertion tube, for capturing images of areas of an inner surface of the cavity at multiple, respective viewing angles;

an orientation sensor, which is arranged to generate a signal indicative of an orientation of the viewing angles of the images; and a control unit, which is coupled to receive the images and the signal, and to map the areas of the inner surface by combining the images responsively to the respective viewing angles.

The present invention will be more fully understood from the following detailed description of the embodiments thereof, taken together with the drawings in which:

DETAILED DESCRIPTION OF EMBODIMENTS

Figure 1:
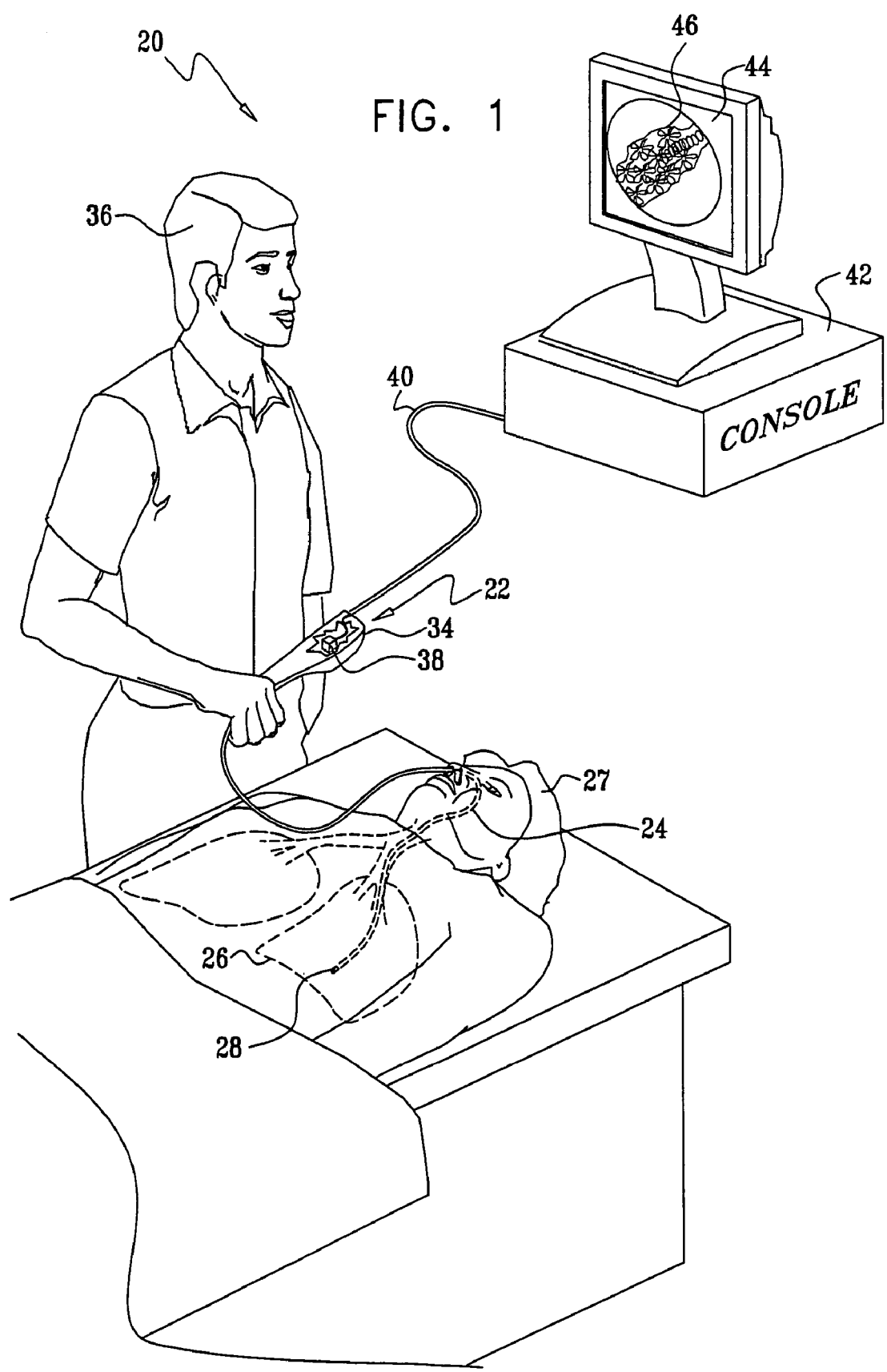
FIG. 1 is a schematic, pictorial illustration of a system for endoscopy, in accordance with an embodiment of the present invention.

FIG. 1 is a schematic, pictorial illustration of a system 20 for endoscopy, in accordance with an embodiment of the present invention. In this example, system 20 is used for bronchoscopic inspection of a lung 26 of a patient 27. In other embodiments, similar systems may be used in other fields of endoscopy, particularly cystoscopy, renoscopy and gastro-intestinal endoscopy, as well as in minimally-invasive surgery. System 20 comprises an endoscope 22, which comprises an insertion tube 24. An operator 36, typically a physician, manipulates the insertion tube using controls (not shown) on a handle 34 at the proximal end of endoscope 22. The operator thus advances a distal end 28 of the insertion tube into a body cavity, such as a bronchial passage in lung 26, and maneuvers the distal end within the lung.

Figure 2:
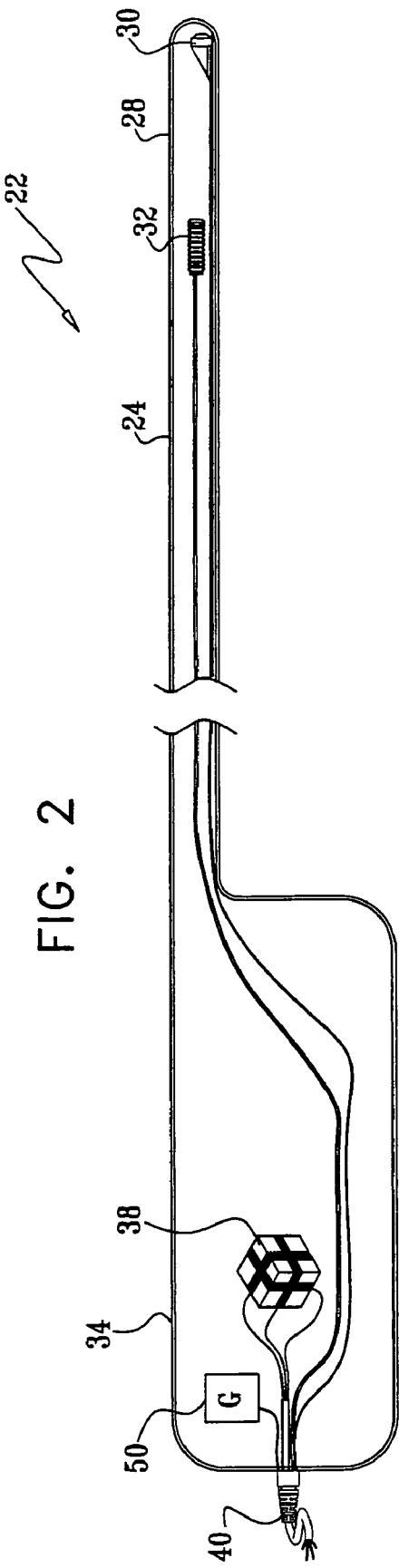
FIG. 2 is a schematic, sectional view of an endoscope, in accordance with an embodiment of the present invention.

FIG. 2 is a schematic, sectional view of endoscope 22, in accordance with an embodiment of the present invention. Distal end 28 of insertion tube 24 comprises an imaging assembly 30, for capturing images in the area of the distal end, inside lung 26. The imaging assembly typically comprises an image sensor, with objective optics that form an image of the region outside distal end 28 on the sensor. Typically, endoscope 22 also comprises a light source, for illuminating the region outside the distal end, as well as other functional elements. The image sensor and other imaging-related elements of endoscope 22 are omitted from the figures for the sake of simplicity, but such elements are well known in the art. Endoscopic imaging elements of this sort are described, for example, in PCT publication WO 03/098913, whose disclosure is incorporated herein by reference. Alternatively, optical images may be conveyed from distal end 28 via relay optics, such as a fiberoptic bundle, to an image sensor at the proximal end of the endoscope.

Video signals generated by imaging assembly 30 are conveyed via a cable 40 to a console 42, which processes the signals to generate an image 46 on a display 44 (FIG. 1). The console may rotate image 46 depending on the orientation angle of distal end 28, as described hereinbelow.

As shown in FIG. 2, endoscope 22 comprises a distal field transducer 32 in distal end 28 and a proximal field transducer 38 at the proximal end of insertion tube 24, inside handle 34. In this embodiment, transducers 32 and 38 are assumed to be magnetic field transducers, which are produced by winding an electrical coil on a suitable core. Typically, transducer 38 serves as the field transmitter, while transducer 32 serves as the field receiver. In other words, console 42 drives a current through transducer 38 via cable 40 in order to generate a magnetic field, which causes a current to flow in transducer 32. Alternatively, transducer 32 may serve as the transmitter, and transducer 38 as the receiver. In either case, the current flowing in the receiver is proportional to the distance between transducers 32 and 38 and to the relative orientations of the transducers.

Console 42 measures the current flowing in the receiving transducer and uses the current value to determine the orientation angle of transducer 32 relative to transducer 38, and thus to determine the orientation of distal end 28 relative to handle 34. In order to measure the orientation unambiguously, it is desirable that transducer 38 comprises multiple coils, which generate spatially-distinct magnetic fields. For example, transducer 38 may comprise three coils wound on orthogonal axes, as shown in FIG. 2. Assuming that transducer 38 serves as the transmitter, console 42 typically drives the coils with waveforms selected so that the currents generated in transducer 32 due to the magnetic fields of the different transmitter coils are distinguishable by the console on the basis of time-, frequency- or phase-domain multiplexing. A position sensing system of this sort is described, for example, in U.S. Pat. No. 6,484,118, whose disclosure is incorporated herein by reference.

Typically, transducer 32 comprises only a single coil, so as to minimize the space required by the transducer within distal end 28 and hence to minimize the diameter of insertion tube 24. Alternatively, for enhanced accuracy, transducer 32 may comprise multiple coils. For example, transducer 32 may comprise three mutually-orthogonal coils, as described in U.S. Patent Application Publication US 2002/0065455 A1, whose disclosure is incorporated herein by reference. Further alternatively, the receiving transducer may comprise a Hall effect transducer or another sort of antenna. Other sorts of magnetic field transmitters and receivers, as are known in the art, may also be used.

In other embodiments, transducers 32 and 38 transmit and receive energy fields of other sorts. For example, the transducers may transmit and receive ultrasonic fields. In this case, console 42 may use the strength and/or phase of the received ultrasonic signals in order to determine the orientation of distal end 28 relative to handle 34.

Optionally, endoscope 22 also comprises an orientation sensor 50 in handle 34. Sensor 50 generates signals that are indicative of the orientation of handle 34 in an external frame of reference. For example, sensor 50 may comprise an inertial sensor, such as an accelerometer or gyroscope. The output of this sensor may be used by console 42 to determine the orientation of handle 34 relative to the earth's gravitational field, as well as sensing movement of the handle relative to its initial position and orientation at the beginning of the endoscopic procedure. Alternatively, sensor 50 may be used to determine the orientation of handle 34 relative to one or more reference transducers (not shown), which are fixed in an external frame of reference outside the body of patient 27. For example, sensor 50 may receive magnetic, optical or ultrasonic energy from the reference transducers, or it may transmit such energy to the reference transducers. The reference transducers may be fixed to objects in the room in which the endoscopic procedure is taking place, such as the walls, ceiling or table on which patient 27 is lying. Alternatively, the reference transducers may be fixed to patient 27 or to operator 36, so that the handle orientation is determined relative to the patient or operator. In any case, console 42 processes the received energy signals from sensor 50 or from the reference transducers (if sensor 50 is configured as a transmitter) in order to determine the orientation of handle 34.

Figure 3:
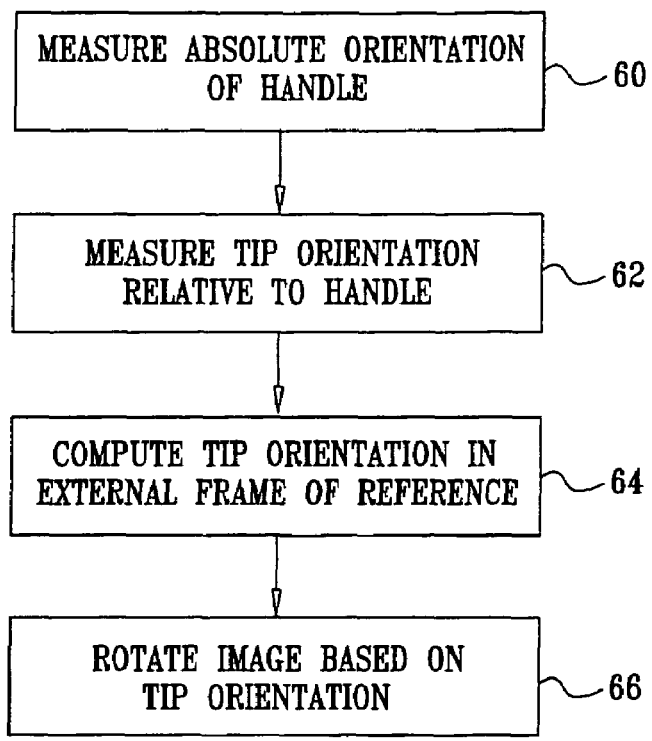
FIG. 3 is a flow chart that schematically illustrates a method for rotating an image based on the measured orientation of the distal end of an endoscope, in accordance with an embodiment of the present invention.

FIG. 3 is a flow chart that schematically illustrates a method for rotating image 46 based on the measured orientation of distal end 28 of endoscope 22, in accordance with an embodiment of the present invention. To determine the actual orientation angle of distal end 28 relative to an external frame of reference, the absolute orientation angle of handle 34 relative to this external frame is first measured, at a handle orientation measurement step 60. Typically, the handle orientation is measured using sensor 50, as described above. The orientation of distal end 28 is measured relative to handle 34 using transducers 32 and 38, at a tip orientation measurement step 62. Step 62 may occur before, after or simultaneously with step 60, and these steps are typically repeated continually in the course of a given endoscopic procedure.

Based on the orientation angles measured at steps 60 and 62, console 42 calculates the orientation of distal end 28 in the external frame of reference, at an orientation computation step 64. Typically, the orientation of the distal end is determined by vector addition of the handle and distal end orientations determined at steps 60 and 62. Alternatively, steps 60 and 64 may be eliminated, and the relative orientation found at step 62 may be used in the step that follows.

Console 42 rotates image 46 to compensate for the orientation of distal end 28, at an image rotation step 66. It is generally sufficient for this purpose that the orientation angle of distal end 28 be measured to an accuracy of a few degrees. Typically, the console rotates the image so that it is oriented in the same direction as patient 27, i.e., so that the right and left directions in the image correspond correctly to the right and left directions within the patient's body. Since it is generally the left/right orientation that is of greatest concern to the operator, the three-dimensional vector that represents the spatial orientation of the endoscope may simply be projected onto the frontal plane of the patient, and the image rotated accordingly. Alternatively or additionally, the image may be transformed to correct for distortion (such as foreshortening) of the image when the image plane of the endoscope is not parallel to the frontal plane. Further alternatively or additionally, other image rotation methods and criteria may be applied, as are known in the art.

Figure 4:
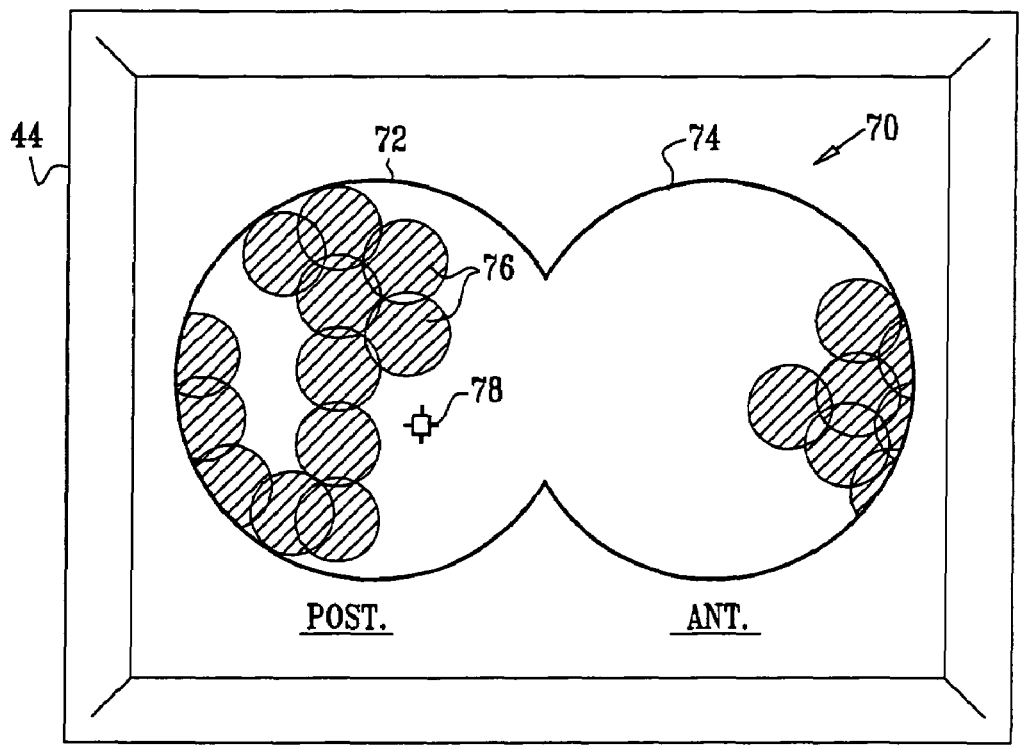
FIG. 4 is a schematic representation of a graphical map shown on a display, in accordance with an embodiment of the present invention.

FIG. 4 is a schematic representation of a graphical map 70 shown on display 44, in accordance with an embodiment of the present invention. This embodiment is useful particularly in imaging the inner surface of a body cavity, such as the bladder, for example. In such applications, operator 36 typically inserts distal end 28 of endoscope 22 into the cavity, and then deflects the distal end over a range of angles in order to image different areas of the surface. It is difficult under such circumstances for the operator to know exactly what areas of the surface he has scanned and whether there are areas that he has missed.

Map 70 assists operator 36 in visualizing the areas that have and have not been scanned by endoscope 22. In this example, the inner surface of the body cavity is represented as the interior of a sphere, which is divided into a posterior hemisphere 72 and an anterior hemisphere 74. Typically, operator 36 presses a button or gives some other input to console 42 to indicate that the imaging scan is to begin. Console 42 then tracks the orientation of distal end 28 within the cavity and accordingly adds a mark 76 to map 70 to represent each area of the surface that has been imaged. A cursor 78 may be used to indicate the current orientation of the distal end of the endoscope on map 70. Using this map, the operator steers the distal end of endoscope 22 so as to image all areas of interest on the inner surface and to identify areas that have not yet been covered.

Console 42 may track distal end 28 and produce map 70 using the relative orientation sensing method described above. Alternatively, other methods of orientation sensing may be used to track the distal end of the endoscope and produce the map. For example, the console may determine the orientation of distal end 28 by sensing the rotation of control knobs or pulleys (not shown) within handle 34 of endoscope 22 that are used in deflecting the distal end. Other methods of orientation sensing that are known in the art, such as magnetic and ultrasonic measurement relative to an external frame of reference, may similarly be used. Furthermore, console 42 may be programmed to control the orientation of distal end 28 automatically, based on the information in map 70, so as to scan the entire inner surface of the body cavity, or to scan a predetermined region of interest within the body cavity.

The method exemplified by FIG. 4 may also be used with endoscopes of other types, including rigid endoscopes. In this latter case, of course, the distal end of the endoscope is not deflected, but it may be rotated, and the endoscope viewing angle may be varied using methods known in the art, such as those described in some of the patents cited in the Background section above. Any suitable method, such as the inertial measurement methods mentioned earlier, for example, may be used to measure the orientation of the endoscope and the viewing angle.

Although the embodiments described above relate to certain particular applications of the present invention in endoscopic imaging, the principles of the present invention may also be used in measuring the orientation of other types of flexible probes, such as catheters. The orientation measurements may be used not only in correcting the orientation of endoscopic images, but also in controlling other types of diagnostic and therapeutic procedures that use flexible invasive probes. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for performing a medical procedure using an invasive probe, which includes an insertion tube having distal and proximal ends manipulable by an operator of the invasive probe, the method comprising:
   determining an orientation of the distal end relative to the proximal end by wireless transmission of an energy field from one of the distal and proximal ends of the insertion tube to the other of the distal and proximal ends; and
   controlling an aspect of the procedure responsively to the orientation.

2. The method according to claim 1, wherein determining the orientation comprises transmitting the energy field from a transmitter in the proximal end and sensing the energy field using a receiver in the distal end.

3. The method according to claim 1, wherein determining the orientation comprises transmitting the energy field from a transmitter in the distal end and sensing the energy field using a receiver in the proximal end.

4. The method according to claim 1, wherein the energy field comprises an electromagnetic field.

5. The method according to claim 1, and comprising inserting the distal end of the probe into a body of a patient, and capturing an image of an area inside the body in proximity to the distal end, wherein controlling the aspect comprises rotating the image responsively to the orientation.

6. The method according to claim 5, wherein determining the orientation of the distal end relative to the proximal end comprises finding a first orientation, and wherein rotating the image comprises finding a second orientation of the proximal end of the probe relative to a predefined frame of reference, and rotating the image responsively to the first and second orientations so as to orient the image relative to the predefined frame of reference.

7. The method according to claim 1, wherein the probe comprises a handle at the proximal end thereof, and wherein determining the orientation comprises finding the orientation of the distal end relative to the handle.

8. Apparatus for performing a medical procedure, comprising:
   an invasive probe, comprising an insertion tube having opposite distal and proximal ends manipulable by an operator of the invasive probe, the probe comprising a transmitter, which is arranged to transmit an energy field, and a receiver, which is arranged to receive the energy field, wherein one of the transmitter and the receiver are disposed at the opposite ends of the insertion tube; and
   a control unit, which is adapted to determine an orientation of the distal end relative to the proximal end responsively to the energy field received by the receiver.

9. The apparatus according to claim 8, wherein the transmitter is disposed in the proximal end of the probe, and the receiver is disposed in the distal end.

10. The apparatus according to claim 8, wherein the transmitter is disposed in the distal end of the probe, and the receiver is disposed in the proximal end.

11. The apparatus according to claim 8, wherein the energy field comprises an electromagnetic field.

12. The apparatus according to claim 8, wherein the distal end of the probe is adapted to be inserted into a body of a patient and comprises an imaging assembly, which is arranged to capture an image of an area inside the body in proximity to the distal end, and
   wherein the control unit is adapted to rotate the image responsively to the orientation.

13. The apparatus according to claim 12, wherein the orientation of the distal end relative to the proximal end is a first orientation, and wherein the invasive probe comprises an orientation sensor, which is adapted to determine a second orientation of the proximal end of the probe relative to a predefined frame of reference, and wherein the control unit is adapted to rotate the image responsively to the first and second orientations so as to orient the image relative to the predefined frame of reference.

14. The apparatus according to claim 8, wherein the probe comprises a handle at the proximal end thereof, and wherein the control unit is adapted to determine the orientation of the distal end relative to the handle.

15. Apparatus for endoscopy, comprising:
   an endoscope, which comprises:
   an insertion tube, having distal and proximal ends;
   an imaging assembly within the distal end of the insertion tube, for capturing images of objects in proximity to the distal end;
   a handle, fixed to the proximal end of the insertion tube; and
   a field transmitter and a field receiver, one disposed within the handle and the other disposed within the distal end of the insertion tube;
   a display, for displaying the images captured by the imaging assembly; and
   a control unit, which is coupled to drive the field transmitter to transmit an energy field, and is coupled to receive signals from the field receiver responsively to the energy field transmitted by the field transmitter, and which is adapted to determine an orientation of the distal end of the insertion tube relative to the handle based on the signals and to rotate the images responsively to the orientation.

16. A method for imaging a cavity using an endoscope having a distal end and a proximal end, the method comprising:
   inserting the distal end of the endoscope into the cavity;
   manipulating the distal end of the endoscope within the cavity so as to capture optical images of areas of an inner surface of the cavity at multiple, respective viewing angles;
   measuring respective orientations of the viewing angles while capturing the images wherein an orientation is measured by wireless transmission of an energy field from one of the distal and proximal ends of the endoscope to the other of the distal and proximal ends; and
   mapping the areas of the inner surface that have been imaged by the endoscope responsively to the measured orientations.

17. An endoscopic imaging system, comprising:
   an endoscope which comprises:
   an insertion tube, having a distal end and a proximal end, which is adapted to be inserted into a cavity;
   an imaging assembly within the distal end of the insertion tube, for capturing optical images of areas of an inner surface of the cavity at multiple, respective viewing angles;

an orientation sensor, which is arranged to generated a signal indicative of an orientation of the viewing angles of the images wherein an orientation is measured by wireless transmission of an energy field from one of the distal and proximal ends of the insertion tube to the other of the distal and proximal ends; and a control unit, which is coupled to receive the images and the signal, and to map the areas of the inner surface by combining the images responsively to the respective viewing angles.

* * * * *